(12) United States Patent
Seguin

(10) Patent No.: US 9,360,493 B1
(45) Date of Patent: *Jun. 7, 2016

(54) MULTI-CHANNEL ASPIRATING AND DISPENSING INSTRUMENT

(71) Applicant: Dan Seguin, Amherst, NH (US)

(72) Inventor: Dan Seguin, Amherst, NH (US)

( * ) Notice: Subject to any disclaimer, the term of this patent is extended or adjusted under 35 U.S.C. 154(b) by 5 days.

This patent is subject to a terminal disclaimer.

(21) Appl. No.: 14/491,110

(22) Filed: Sep. 19, 2014

Related U.S. Application Data

(62) Division of application No. 12/776,558, filed on May 10, 2010, now Pat. No. 8,899,118.

(51) Int. Cl.
*G01N 35/10* (2006.01)
*B01L 3/02* (2006.01)

(52) U.S. Cl.
CPC .......... *G01N 35/1074* (2013.01); *B01L 3/0217* (2013.01); *B01L 2200/021* (2013.01); *B01L 2200/0689* (2013.01); *G01N 2035/103* (2013.01)

(58) Field of Classification Search
CPC ................. G01N 35/1074; G01N 2035/103; B01L 3/0217; B01L 2200/021; B01L 2200/0689
See application file for complete search history.

(56) References Cited

U.S. PATENT DOCUMENTS

| | | | | |
|---|---|---|---|---|
| 3,525,264 A | * | 8/1970 | Cybulsky | A61M 1/00 422/501 |
| 4,976,161 A | * | 12/1990 | Czernecki | B01L 3/0227 422/926 |
| 5,052,697 A | * | 10/1991 | Ishikawa | F16J 15/43 277/410 |
| 6,102,984 A | * | 8/2000 | Carl | G01N 35/028 73/864.24 |
| 2006/0071973 A1 | * | 4/2006 | Peeters | B01L 3/0268 347/54 |

* cited by examiner

*Primary Examiner* — Daniel S Larkin
*Assistant Examiner* — Alex Devito
(74) *Attorney, Agent, or Firm* — Luis Figarella

(57) ABSTRACT

A pipette receiver and its variations are discussed for use in a multi-channel pipetting device typically used for medical, biological or biochemical research and development. There is a plurality of individual positive air displacement channels that are fitted to individual disposable pipette tips intended to pipette into associated "plates". These "plates" may be Micro-titer plates, wells or vials each typically containing 96 wells in an 8×12 array usually spaced 9 mm apart. Other common plates contain 384 wells 4.5 mm apart in the same footprint of the 96, or a 1536 well plate fitting the same footprint.

2 Claims, 16 Drawing Sheets

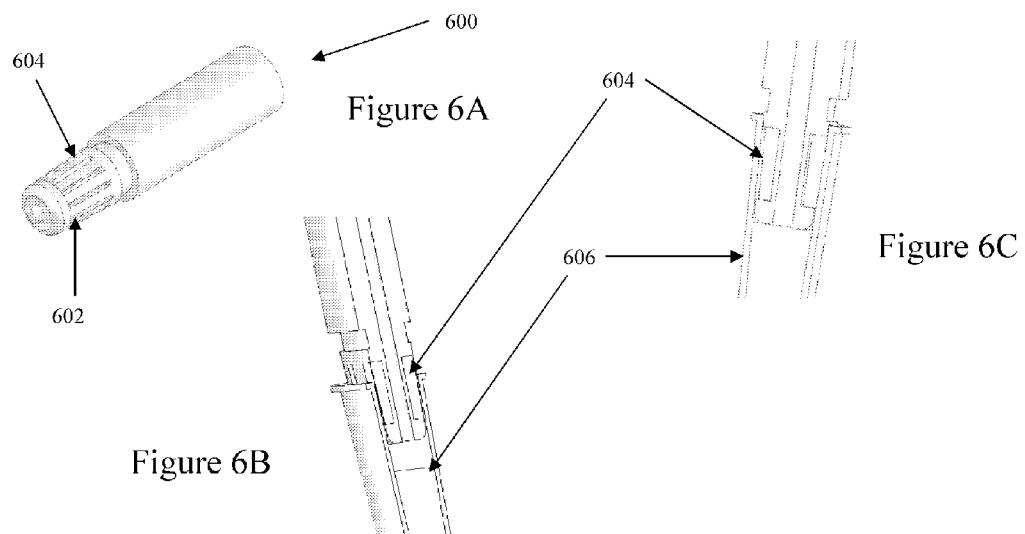
Figure 6A
Figure 6B
Figure 6C
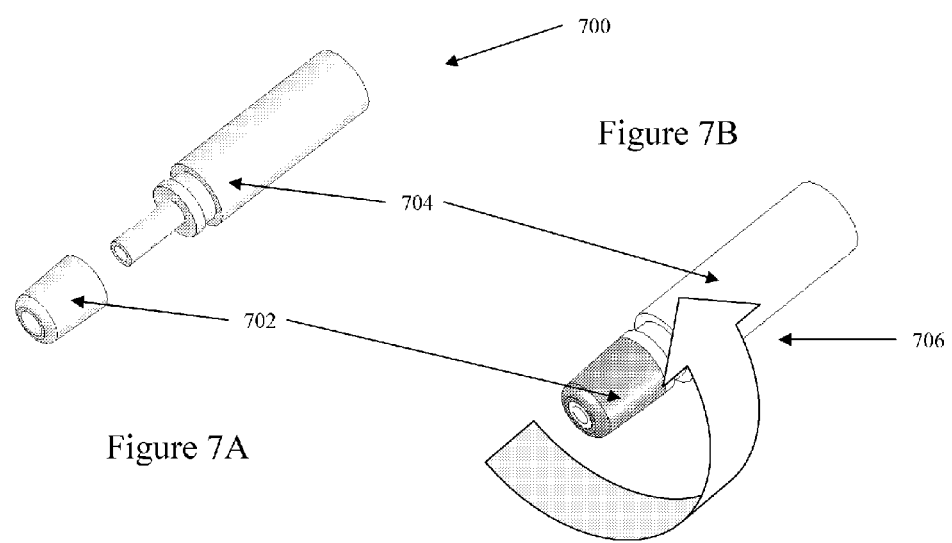
Figure 7A
Figure 7B

MULTI-CHANNEL ASPIRATING AND DISPENSING INSTRUMENT

CROSS-REFERENCE TO RELATED APPLICATIONS

This application is a Divisional of pending U.S. patent application Ser. No. 12/776,558 titled "Multi-Channel Aspirating and Dispensing Instrument"," filed on May 10, 2010, the disclosure of which is herein incorporated by reference in its entirety.

TECHNICAL FIELD

The present invention relates generally to multi-channel aspirating and dispensing pipettors, and in particular, those having repositionable tip fittings or mounting shafts for disposable pipette tips.

BACKGROUND

In laboratory work, multi-channel pipettors are designed to enable laboratory workers to transfer multiple samples or reagents from one series of containers to another series of containers, such as from one set of wells in a micro titer plate to another micro titer plate. Multichannel liquid aspirating & dispensing instruments, or pipettors, capable of aspirating and dispensing single or multiple channels at a time, typically 1, 8, 12, 96, 384 & 1536 channels at a time and moving to a plurality of microplate stations. Many multi-channel pipettors rely on electronically controlled stepper motors to control piston movement for aspirating and dispensing.

The spacing between individual channels is fixed to accommodate the ANSI SBS microplate standards. Precision and accuracy, especially in dispensing, are the basic driving specifications required by those in the biological sciences laborites. Values of <10% at volumes down to 1 micro liter are considered good.

Thus the market is left with single row manual or powered units, or instruments that are big, heavy & expensive as they are intended to be used in an automated environment. What is required is a portable, semi or fully automated multi-channel pipettor that overcomes the many complications and limitations of the previous systems.

SUMMARY OF THE INVENTION

This section is for the purpose of summarizing some aspects of the present invention and to briefly introduce some preferred embodiments. Simplifications or omissions may be made to avoid obscuring the purpose of the section. Such simplifications or omissions are not intended to limit the scope of the present invention.

In one aspect, the invention relates to fittings and receivers for holding pipettes on aspirating and dispensing systems. In one embodiment, to a pipette holding apparatus comprising a proximal annular shape designed to make continuous contact with a pipette's internal surface at the proximal end of said pipette, one or more annular shapes designed to make continuous contact along the length of a pipette's internal surface, said annular shapes being of sequentially reduced diameter, with the one at the distal end having the smallest diameter, and a cavity between said sequential annular shapes designed to avoid contact with a pipette's internal surface.

In one embodiment, to an apparatus where two or more annular shapes are arranged as substantially continuous horizontal bulges, and the cavity between them forms a in a gradual spool-like shape. In one embodiment, to an apparatus with two or more annular shapes arranged as substantially continuous horizontal loops, with significantly sharp walls, and the cavity between them forms a significantly sharp walled air gap between them. In another aspect, to an apparatus wherein the walled air gap between the two continuous horizontal loops is divided into two or more sections by the addition of one or more barrier travelling along the length of the axis of insertion, and the barrier diameter matches that of the two or more annular shapes they connect.

In another aspect, the invention relates to a pipette holding apparatus comprising a proximal annular shape designed to make significantly continuous contact with a pipette's internal surface at the proximal end of said pipette, one or more compressible vanes of a diameter slightly larger than the pipette's inner orifice diameter, arranged so that the vanes travel significantly in the direction of the axis of insertion, and one or more cavities between the vanes.

In another aspect, the invention relates to a pipette holding apparatus comprising a Ferro fluidic taper expansion with a magnetic field and magnetic means to radially expand said Ferro fluidic filled lower tapered fitting so that an annular shape is formed in said taper that makes continuous contact with a pipette's internal surface at the proximal end of said pipette.

In another aspect, to a pipette holding apparatus comprising an upper stationary fitting, a pull/push rod having axial movement in/out of the fitting, a compliant tapered head, mechanical means for pulling on said rod, so that when the rod pushes on the head, its diameter expands outward into the pipettes' internal surface, forming a continuous annular seal; and mechanical means for pushing on said rod.

In one aspect, the invention relates to a pipette holding apparatus comprising an upper stationary fitting, a pull/push rod having axial movement in/out of the fitting, a compliant tapered head receiver, mechanical means for pulling on said rod, so that when the rod pushes on the head, its diameter expands outward into the pipettes' internal surface, forming a continuous annular seal and mechanical means for pushing on said rod. In one embodiment, the apparatus comprises a compliant tapered head receiver has one or more slits cut along a portion of its side, and the pull/push rod has a tapered head at one end.

In one aspect, the invention relates to a multi-channel aspirating and dispensing system comprising a single motor to drive the pump and the pipette ejecting mechanism, electronic means for controlling the aspiration and dispensing functions, a multilevel stepped plate that eject smaller groups of tips at a time. In one embodiment, there is an adaptor to accommodate 384 well micro titer plates with a 96 channel pipetting head, said adaptor requiring three easy manual X-Y movements to target all 384 wells. In another embodiment, the X-Y movements are halved, allowing the adaptor to accommodate 384 channel pipettor and a 1536 well micro titer plate.

Other features and advantages of the present invention will become apparent upon examining the following detailed description of an embodiment thereof, taken in conjunction with the attached drawings.

BRIEF DESCRIPTION OF THE DRAWINGS

FIGS. 6A-6C are views of proposed fittings, according to illustrative embodiments of the invention.

FIGS. 7A-7B are views of proposed magnetic fittings, according to illustrative embodiments of the invention.

DETAILED DESCRIPTION

To provide an overall understanding of the invention, certain illustrative embodiments will now be described, including apparatus and methods for displaying images. However, it will be understood by one of ordinary skill in the art that the systems and methods described herein may be adapted and modified as is appropriate for the application being addressed and that the systems and methods described herein may be employed in other suitable applications, and that such other additions and modifications will not depart from the scope hereof.

Figure 1:
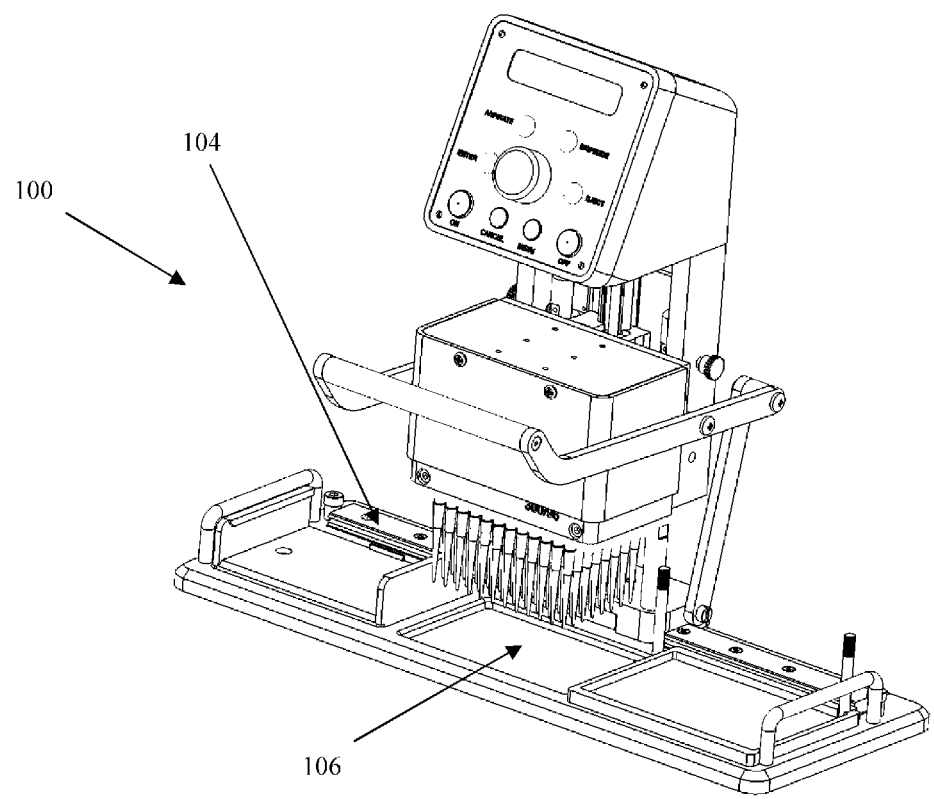
FIG. 1 is a perspective view of the multi-channel aspiration and dispensing system, according to an illustrative embodiment of the invention.

FIG. 1 is an isometric view of a multi-channel liquid aspirating & dispensing instrument, according to an illustrative embodiment of the invention. The design provides a lightweight, portable instrument that can fit into a standard lab hood or be moved around the lab with ease, yet have the same accuracy and precision standards found in semi-automated and high end fully automated pipettors. The design uses a single motor which drives the pump & eject pipette tips. This is accomplished using a smaller, low cost motor & linear rail assembly 1502. Motion to the three dimensions of movement is manual, eliminating motors & controls to lower cost & weight. It also simplifies operation as no external software, controller or computer is required.

Mechanically this instrument provides easy & precise horizontal and vertical motion using guided rails and shafts 104. All manual motion is intended to be done effortlessly. The vertical motion carries the weight of the mechanical components using a precisely counterbalanced gas spring. The base of the instrument is heavier than everything above to eliminate the tendency to tip. In one embodiment, an optional LED light is available to light up the area above the active plate position 106.

In one embodiment, the horizontal & vertical dimensions are designed to fit into any typical laboratory fume hood without modifications. The general dimensions for a 3-station model are 17.78 cm wide×45.72 cm long×40.64 cm high. This footprint can easily fit on top of available counter space. A user can now bring the pipettor to the work area rather than having the work area brought to the pipettor.

Figure 2:
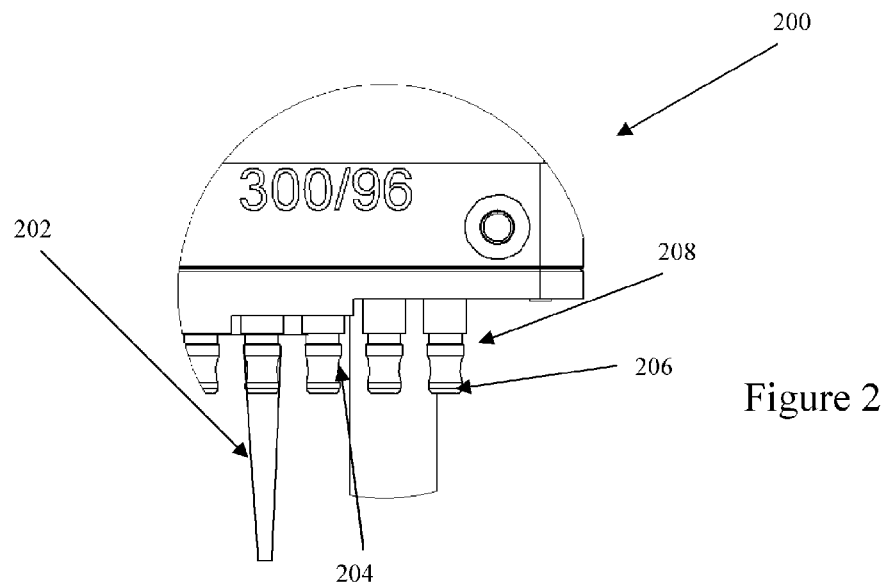
FIG. 2 is a close-up view of the fitting and pipette, according to an illustrative embodiment of the invention.

As seen in an isometric close-up 200 (in FIG. 2), the disposable pipette tip 202 needs to be inserted and sealed onto the individual pipette fitting channel 204. When doing 96 or 384 tips at a time, the manual force required to press these all on at the same time is significant. In one embodiment, the invention is capable of doing the above at speed and with minimal effort through the unique fitting design 206 and 208.

Figure 3:
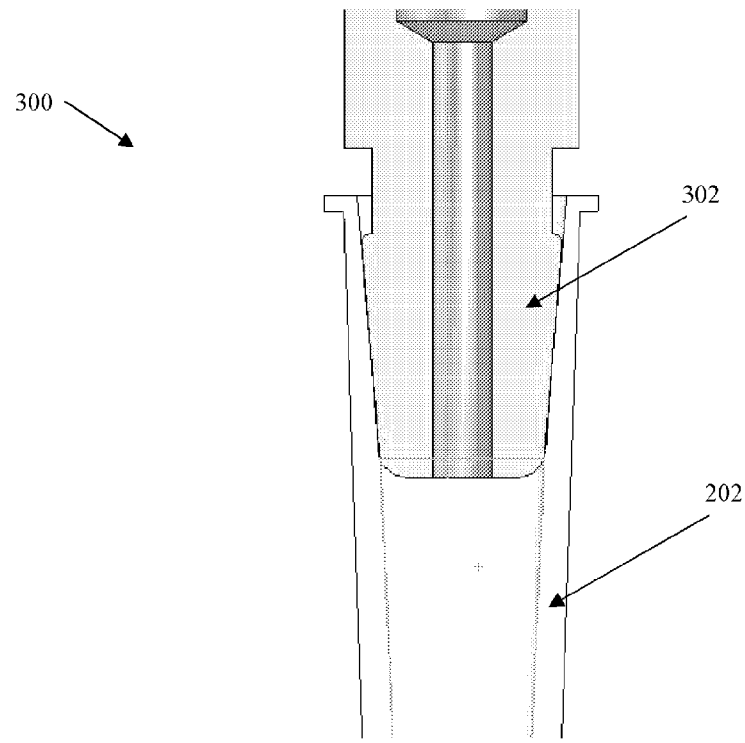
FIG. 3 is a cross-section of the conventional fitting, according to an illustrative embodiment of the invention.

In previous inventions, as shown in (FIG. 3) a straight cross sectional view 300 of a standard fitting 302 has a line-to-line fit with the pipette tip 202, which is typically pressed over a complementary similar shaped parallel surface. This provides an air tight seal. The force to insert this is in the range of one to two kilograms. For a typical 96 style configuration as described previously, the cumulative force would be 96 to 192 Kgs, and would be too much for most people to achieve.

Figure 4:
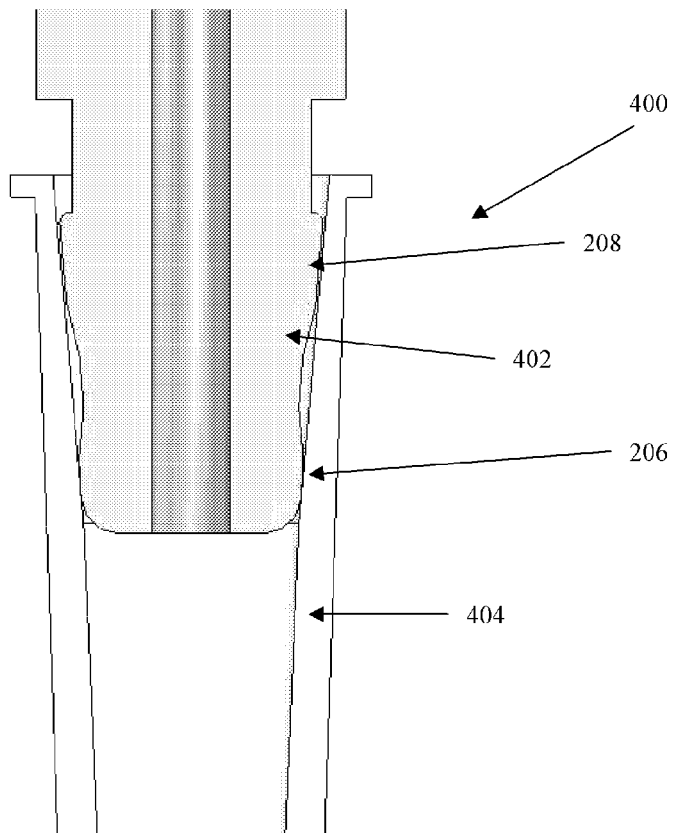
FIG. 4 is a cross-section of a proposed spool-like fitting, according to an illustrative embodiment of the invention.

As seen in FIG. 4, in one embodiment 400, the proposed new fitting requires less than ¼ Kg. per tip, equating to less than 24 Kgs. This reduced force is accomplished by the spool-like surface of the fitting 402, limiting the contact area between the traditional straight inside wall of the pipette tip 404 and the two smaller areas at the top 208 and another at the bottom 206. This makes the pressure required to make an airtight seal between the inside wall of the tip 404 and fitting 402 is accomplished with less force. Mathematically explained, pressure=force/area, with a constant pressure a lower contact area yields a lower force. Further force reduction is accomplished by using a fitting material having low friction properties. Further force reduction is accomplished by the mechanical advantage of the pivotal linkage and handle 1910.

The contact area is split into two regions 206 and 208, in one embodiment spread apart as far as possible to provide tip stability. If the reduced contact area were localized, then the tip would tend to act more like a pivotal joint. Having two contact areas spread apart stabilizes the tip against perpendicular forces, such as the bottom distal tip end touching the side of the plate well. The two points of contact further apart provide increased lateral stability.

Figure 5B:
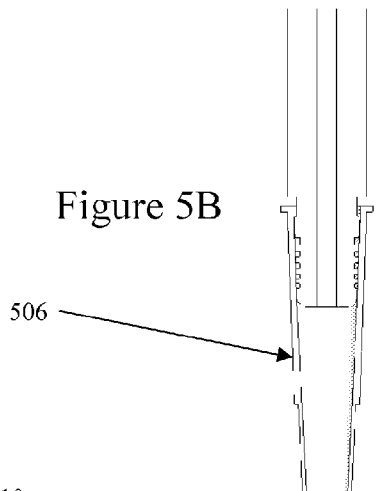
FIGS. 5A-5C are views of proposed improved fittings, according to illustrative embodiments of the invention.
Figure 5A:
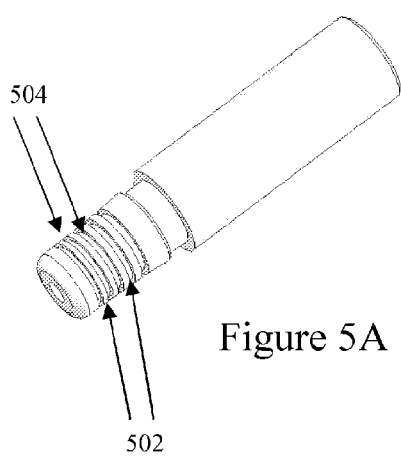
Figure 5C:
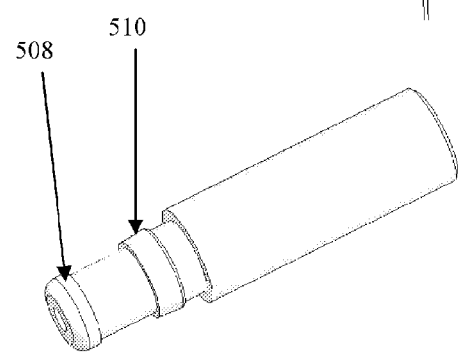

FIGS. 5A-5C illustrate a number of alternate exemplary embodiments to accomplish the same goal by modifying a fitting to create air gaps, and variations of the gap seen in the fitting 402, creating low force fittings. The two or more horizontal rings 502 provide one or more interposed air gaps 504 that limit contact area with the pipette tip 506. This limited contact requires less force to insert said pipette tip 506 onto any fitting. In an alternate embodiment, spool designs 508, 510 having sharper transitions also accomplish a low insertion force. As seen in FIGS. 6A-6C in alternate embodiment 600, vertical gaps 602 traveling significantly along the direction of the axis of insertion create the air gaps 604 and provide a stable surface for a pipette tip 606. In an alternate embodiment, the air gaps may travel in a spiral direction.

FIGS. 7A-7B illustrate an exemplary illustration of an alternate embodiment 700, where a Ferro fluidic taper expansion utilizing a magnetic field is used to radially expand the Ferro fluidic filled lower tapered fitting 702. The taper expansion would be powered by the fitting impale command generated by the user interface. The lower fluid fitting 702 is bonded to the upper fitting 704 to form a permanent assembly of the two parts 706. The magnetic field required to change the lower fitting 702 may be generated by using either a movable permanent magnet or energizing an electromagnet. The field is then passed through a "tuned" iron rod within the upper fitting, or it may be the entire upper fitting is iron with a protective coating.

Figure 8:
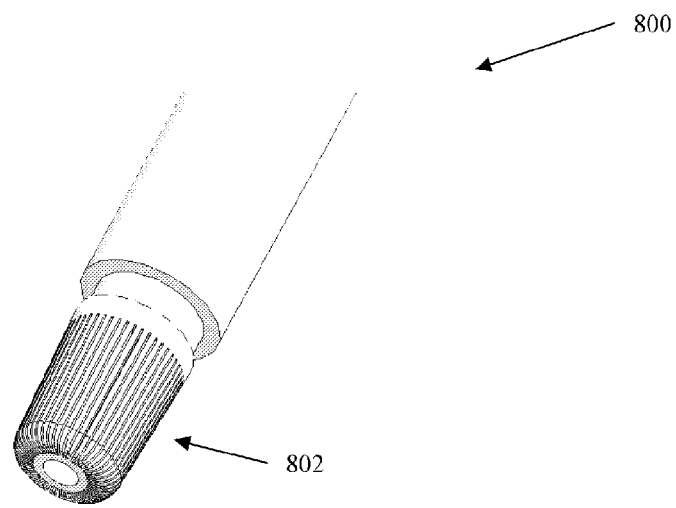
FIG. 8 is a view of a compressible fitting, according to an illustrative embodiment of the invention.
Figure 9:
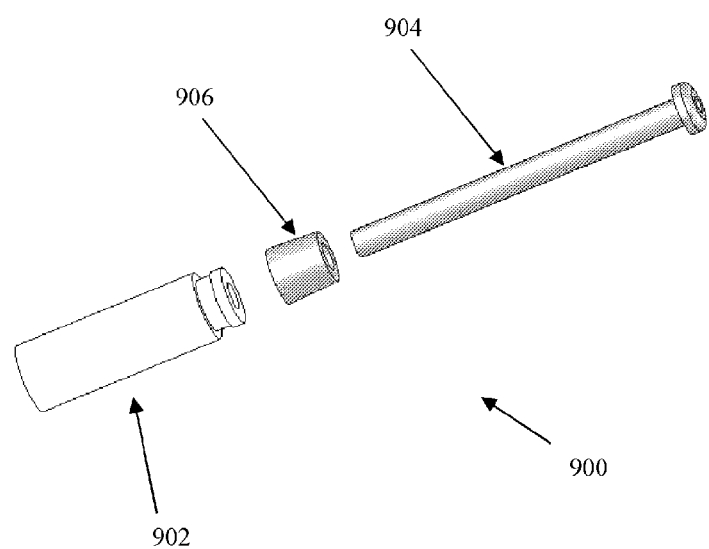
FIG. 9 is a views of a tapered compressible fitting, according to an illustrative embodiment of the invention.
Figure 10A:
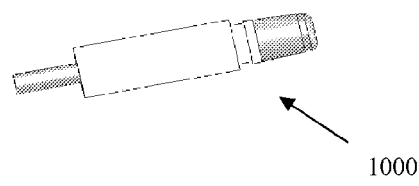
FIGS. 10A-10D, 11-12, 13A-13C, 14A-14B are views of a tapered compressible fitting, according to illustrative embodiments of the invention.
Figure 10B:
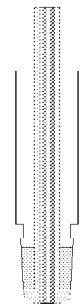
Figure 10C:
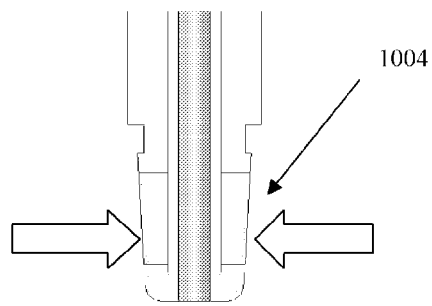
Figure 10D:
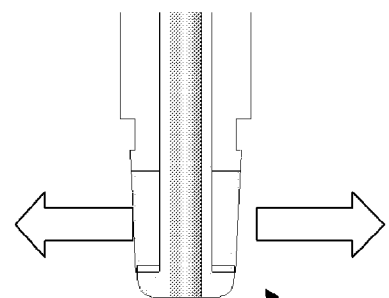
Figure 11:
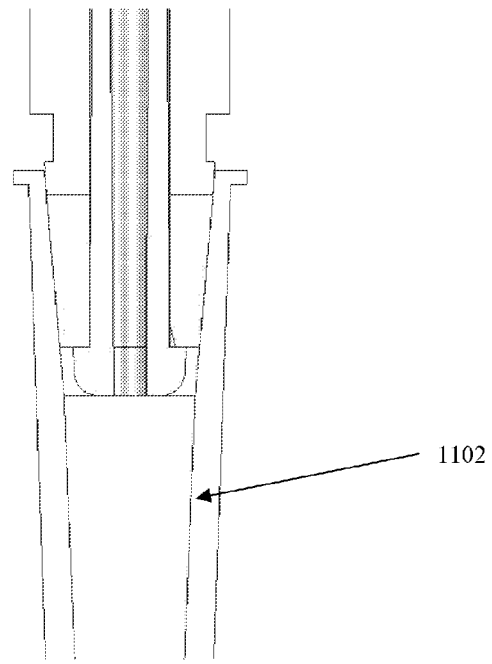
Figure 12:
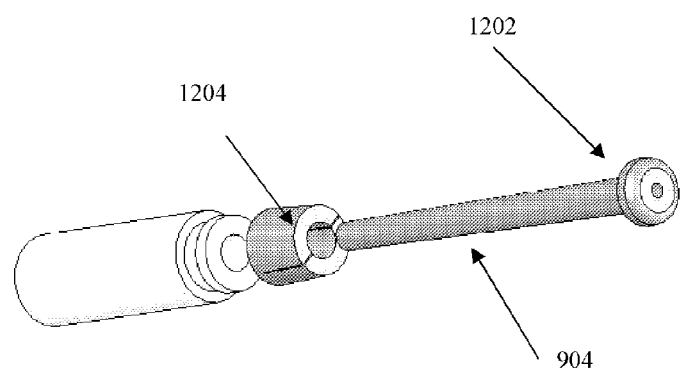
Figure 13A:
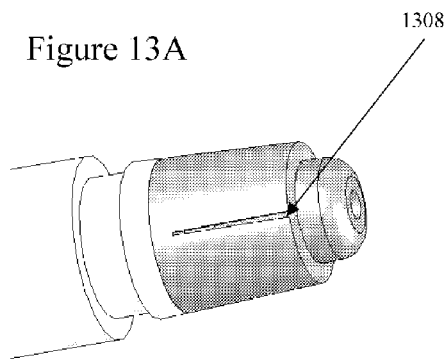
Figure 13B:
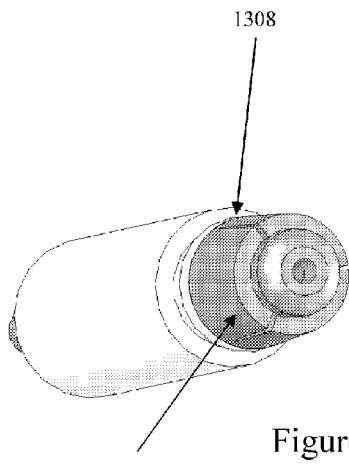
Figure 13C:
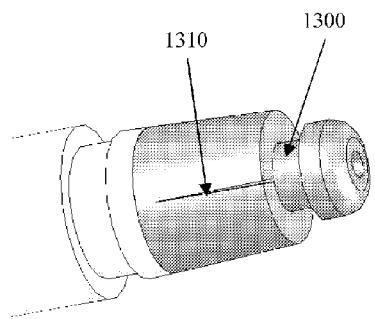
Figures 14A, 14B:
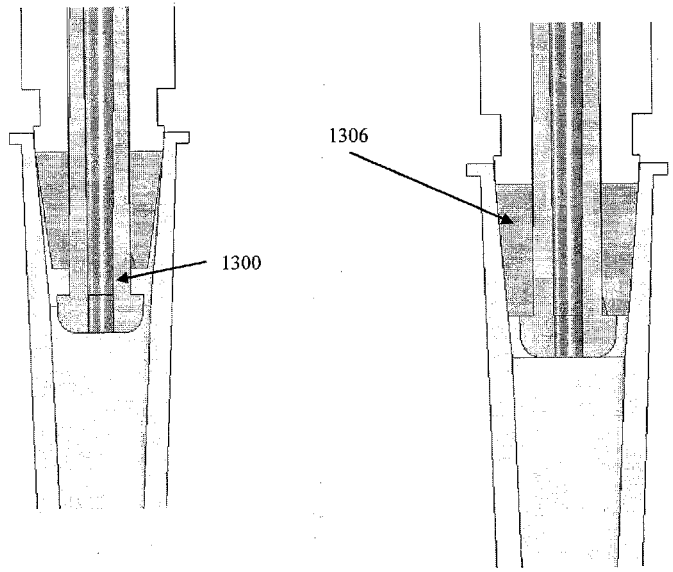
Figure 15:
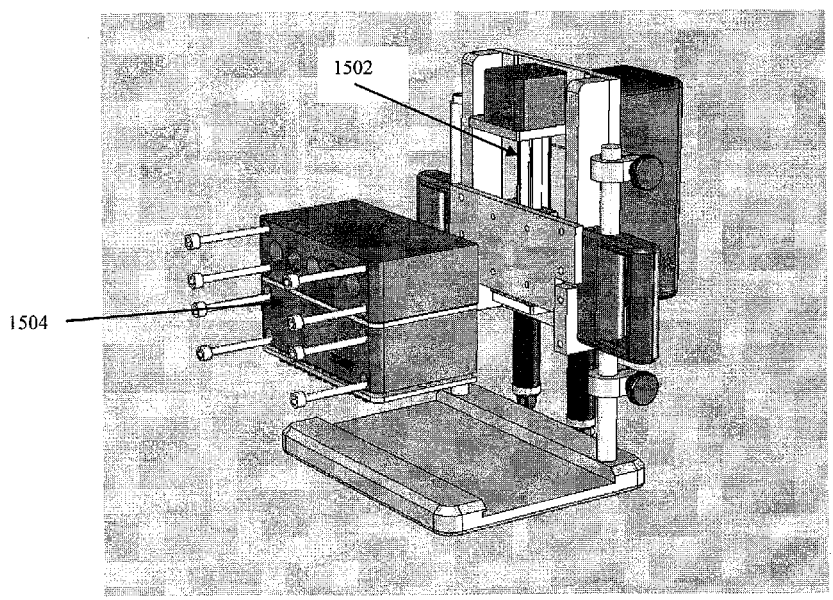
FIGS. 15-18 are isometric perspectives of the system components, according to illustrative embodiments of the invention.
Figure 16:
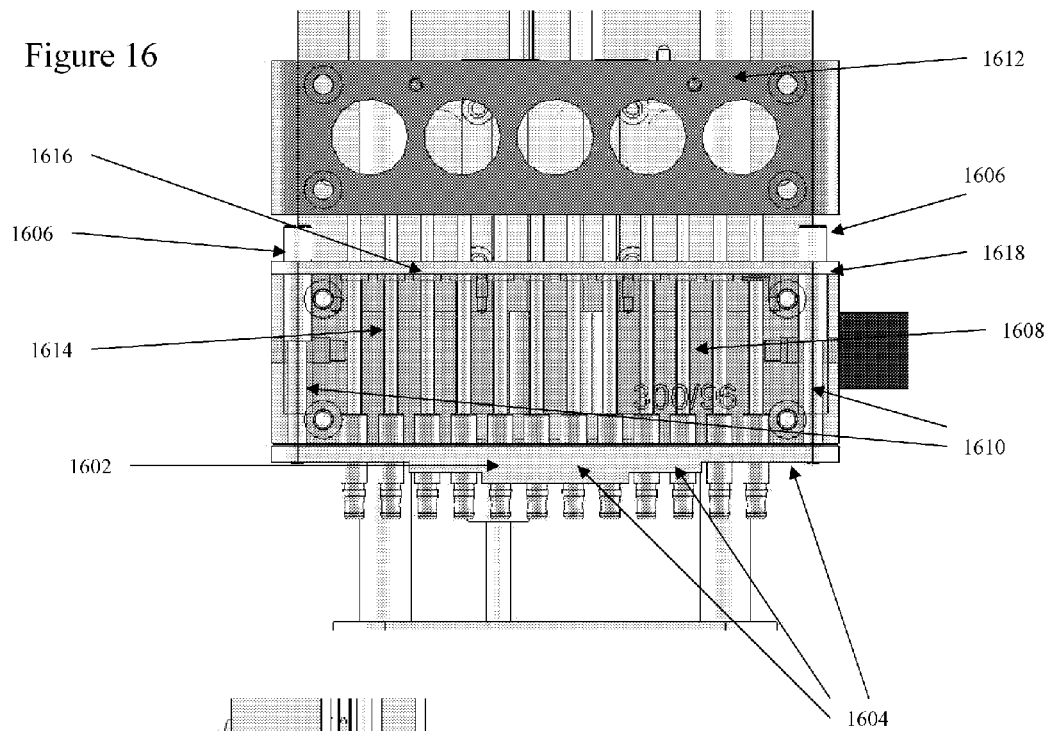
Figure 17:
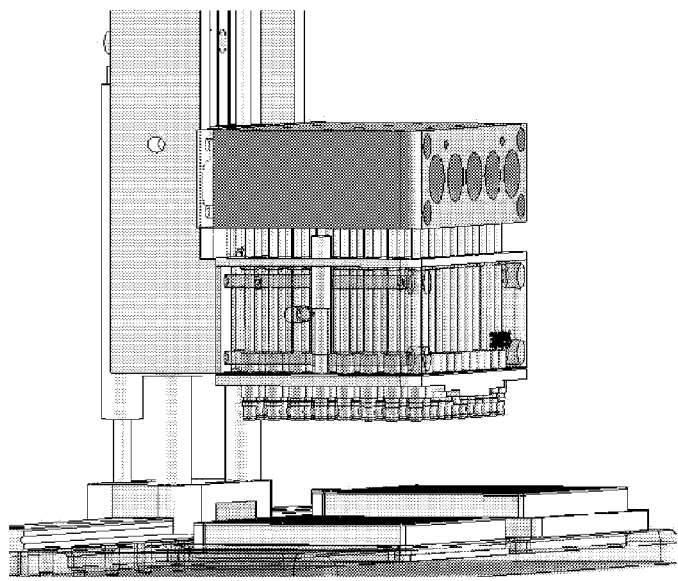
Figure 18:
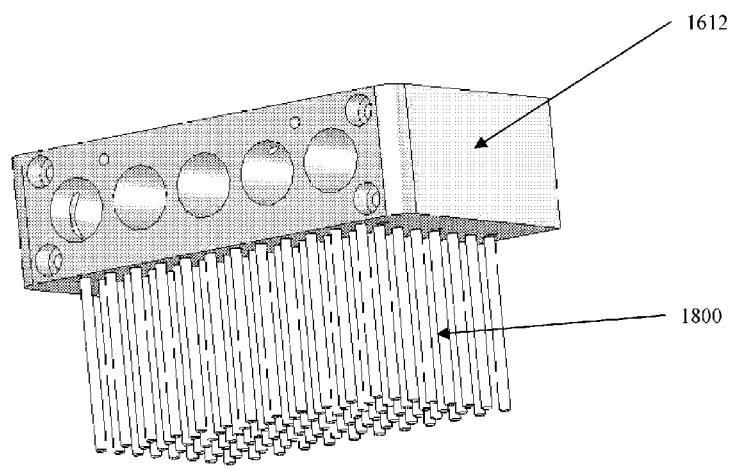

FIG. 8 illustrates an exemplary illustration of an alternate embodiment 800. In it, a flexible compressible fitting 800 is comprised of rubber (be it natural or synthetic), silicone or such other similar compliant material having many vertical vanes or slices 802 (in one embodiment significantly in the direction of the axis of insertion) will allow an easy pipette tip insertion by conforming to the exact taper then giving-way or bending in areas where the press-fit is not uniform. This is especially useful when using a variety of pipette tips from various manufactures where the taper varies. In an alternate embodiment, the vanes have a spiral orientation along the axis of insertion.

(Currently Amended) FIGS. 9, 10A-10D, and 11 illustrate exemplary illustrations of alternate embodiments of a mechanically expanding and contracting taper fitting. The fitting assembly parts 900 look like the standard fitting except it is comprised of three parts, an upper stationary fitting 902, a pull/push rod 904, having axial movement in/out of the fitting and a compliant taper section 906. The pull/push rod 904 when pulled toward the taper section 906 compresses the compliant material making the tapered diameter expand outward 1002. When a non compliant pipette tip is in place, the expanding compliant taper forms a tight seal. To eject the tip the rod 904 moves away from the taper 906 that is fixed to one or two ends. In one embodiment, the pull/push rod movement would be controlled by movement of the rod in connection to the piston assembly 1504 under command of the electronic user interface.

This motion stretches the taper 906, reducing the diameter 1004 and forming a slip fit with the pipette tip 1102. Now the tip can be removed with much ease. Likewise, and more importantly, when in this last position where the taper diameter is less than the pipette tip diameter, one can easily insert a series of 96 tips manually with less than ¼ Kg of force per tip. This ability to manually insert and pick up a series of 96 pipette tips is a key feature that makes this instrument desirable. Once the tips are in place the push/pull rod will move toward the taper forming a press fit making a seal & adding positional stability with the entire pipette tip ID in contact with the fitting. This concept applies to all the fittings discussed throughout this provisional patent.

(Currently Amended) FIGS. 12, 13A-13C, and 14A-14B illustrate exemplary illustrations of alternate embodiments of similar concepts, the pull/push rod 904 is tapered 1202 at one end and the compliant or semi-compliant receiver has one or more slits cut along a significant portion of its length (in the axis of the direction of insertion or length of the receiver), creating a split semi-compliant 1204 taper. When the tapered end 1300 of the pull/push rod 1202 is moved inwardly toward the split taper 1306, the rod will push the split taper radially outward, increasing the effective Outer Diameter (OD) of the taper, since the one or more splits 1308 will allow ease in flexing. When the rod moves away from the taper 1306 then the increasingly smaller Outer Diameter (OD) of the rod's taper 1202 allows the elastic semi compliant taper 1306 to contract causing its OD to decrease 1310 and establish a slip fit with the pipette tip. More importantly, when in this last position where the taper diameter is less than the pipette tip diameter, one can easily insert a series of 96 tips, manually with less than ¼ Kg of force per tip. This ability to manually pick up a series of 96 pipette tips is the key feature that makes this instrument desirable. Once the tips are in place the push/pull rod will move toward the taper forming a press fit making a seal & adding positional stability with the entire pipette tip in contact with the fitting. In one embodiment, the split taper can be made of two or more splits.

FIGS. 15-18 illustrate exemplary embodiments of the mechanism for tip ejection. In one embodiment, Tip Ejection off the fitting is done using the same motorized linear rail assembly 1502 used for pipetting, which moves the ejector plate 1602 up/down. The ejector plate is multileveled and stepped 1604 in order stagger the push of the tips into smaller sections or groups of tips at a time. This results in a reduction in the force to eject, thus requiring a less expensive linear rail assembly, and lowers manufacturing costs.

The plate 1602 is connected to two push rods 1606 that travel up through the cylinder block 1608 and protrude a given distance beyond the top surface of the cylinder block. Two springs 2302 urge the pushrods in an upward direction. The piston block 1612 contacts the two push rods 1606 thus transferring the ejection force to the ejector plate. The piston block triggers a sensor just before touching the push rods, and the electronics deliver a message to travel a precise distance required to remove all tips. This motion is preset and performed at a slow speed to produce a greater force from the electromechanical assembly. Using the electromechanical assembly for ejection also eliminates those forces required by the user, reducing or eliminating potential fatigue as well as potential injuries from repetitive motions, such as carpal tunnel syndrome.

Pipetting accuracy and precision are critical, and usually the most important factors of purchasing a pipettor. In one embodiment, this design uses a precision step motor driven linear rail assembly 1502 with precisely controlled electronics to operate the positive displacement pump chambers. These pump chambers are made by the openings in the cylinder block 1608 being filled by the individual pistons 1800 of the piston block 1612, sealed with O-rings 1616 are compressed between the upper O-ring plate 1618 and the cylinder block 1608 creating the piston assembly 1504. The precise up/down motion of the assembly is key to the repeatability and consistent accuracy of fluid dispense. In operation, the displacement of the piston block up/down is controlled by the motor/rail assembly 1502 (in turn controlled by the system electronics). The controlled motion of the piston block 1612 generates motion of each piston 1800 within each channel 1614 created by the individual openings in the cylinder block 1608. An up motion aspirating fluid into the pipette tip, whereas a down motion compresses air dispensing fluid out of the tip.

In operation, a user starts with a unit 100 having no tips at the fittings 204, and the pistons 1800 at their lowest (all in) position within each channel 1614. The pipette tips are held within a pipette box that slides into and is retained by the pipette box retainer 1912. The complete assembly 1914 is lowered, inserting each pipette 202 into each channel fitting 204. In one embodiment, mechanical means within the channel operate to expand the channel fitting (FIGS. 9-14). In an alternate embodiment the special fitting shape accomplishes the compression 400. In on embodiment, the tip is energized via electromagnetic means to expand the fitting 204 end and hold the tip.

With the tips held, the assembly 1914 is translated along a linear bearing rail 104 to a position with a tray under it whose openings are holding a fluid. The assembly is lowered so the tips are within it, and the aspiration is engaged by the separation of the piston block 1800 from the cylinder block 1608 via the motor/rail displacement. The assembly is again translated, one or more trays are set under it as the fluid is displaced via the lowering of the piston block 1800 into the cylinder block 1608 under the precise control of the electronics.

The operation is repeated until a new set of tips is deemed necessary. At that time, the assembly 1914 is placed on a tip assembly, and the tips ejected via the reverse of the embodiments used.

All the pipetting channels upon which each individual piston 1800 actuates provides the precision or the consistency of dispense between each channel fitting 204. The quality of the electronics and the mechanical linear rail directly coupled to the piston assembly 1504 give this instrument the same accuracy and precision found in much more expensive instruments.

Figure 19:
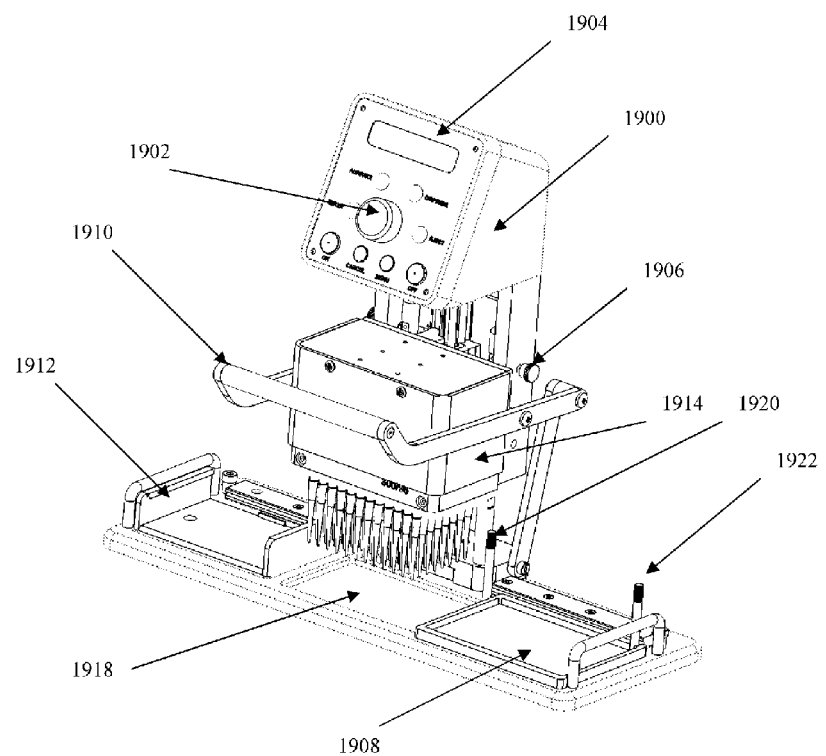
FIGS. 19-26 are various isometric perspectives of the system, according to illustrative embodiments of the invention.

In one embodiment (FIG. 19), electronic controls 1900 provide the embedded step motor controls, a user interface 1902 for programmability and a display area 1904 to visually see commands. In one embodiment, a rotary knob in the center of the control panel turns to select menus, programs, to enter aspirate/dispense volumes and such. Without moving fingers off the knob, a user can push either of the surrounding buttons. This provides an easier method of programming by not having to move your hand away from the center of the panel. The display area provides real time feed back to either programming or running a program. There is an option to choose languages on the display and the control panels are engraved with the associated language.

The overall operation of this instrument is intended to provide continuous easy hands-on motion. Much like an automotive steering wheel having controls built in to keep the drivers hands on the wheel. This instrument has the ability to move horizontally and vertically with little effort without removing your hands from the handle 1910. Once a program is entered and a series of plates are positioned below then one can seamlessly perform desired steps with minimal hand motion.

In one embodiment, a single handle 1910 allows the up/down operation of the pipette assembly for aspirating and dispensing between the tray positions 1908 and 1918. A special tip box holder 1912 may be used to ease operation when picking or ejecting tips, as well as when aspirating and dispensing fluids from one tray to another.

Figure 20:
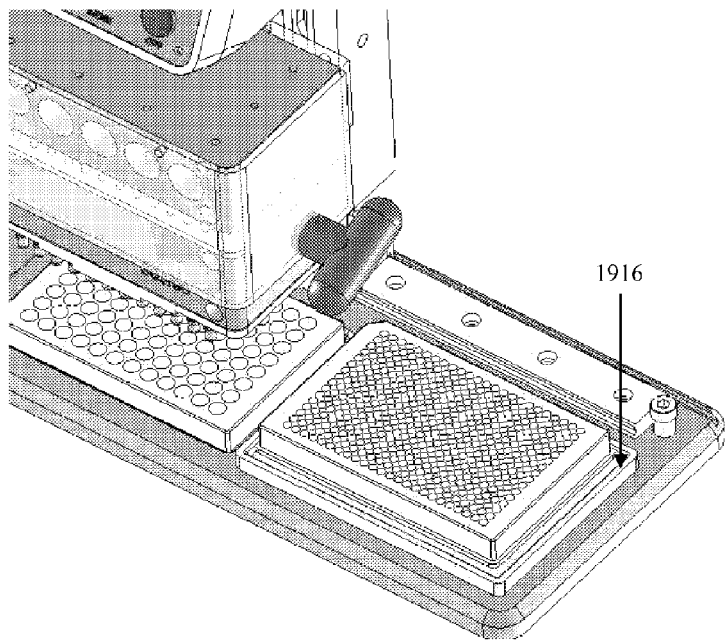

The instrument is intended to be built as a 96 or 384 channel model. However, as seen in (FIG. 20) the less costly 96 channel model can accommodate a 384 well plate by using a 96/384 adaptor 1916. This adaptor's station well is 4.5 mm longer and wider than the ANSI_SBS_4-2004 footprint described in detail in the attached specifications. Since a 384 well is spaced 4.5 mm apart and the 96 is 9.0 mm apart the difference is 4.5 mm. When a 96 channel pipettor is directly over the center of an 384 well, the next well is achieved by sliding the 384 plate from one right edge of the adaptor all the way over to the adjacent left edge (or vice versa). Now the pipettor is directly over the next well in that row. To get to the row below, move the 384 plate from the bottom edge all the way up to the top edge, then repeat the left-right motion to get the last well. Three simple movements allow the 96 channel pipettor to reach all of the 384 wells.

Figure 21:
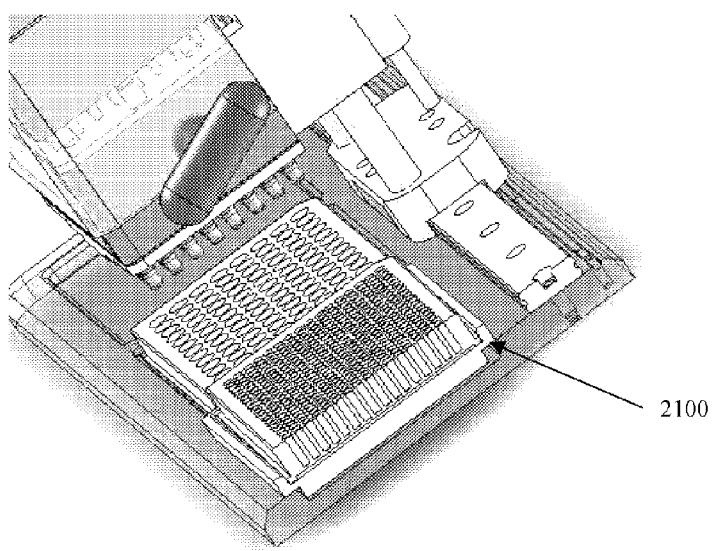
Figure 22:
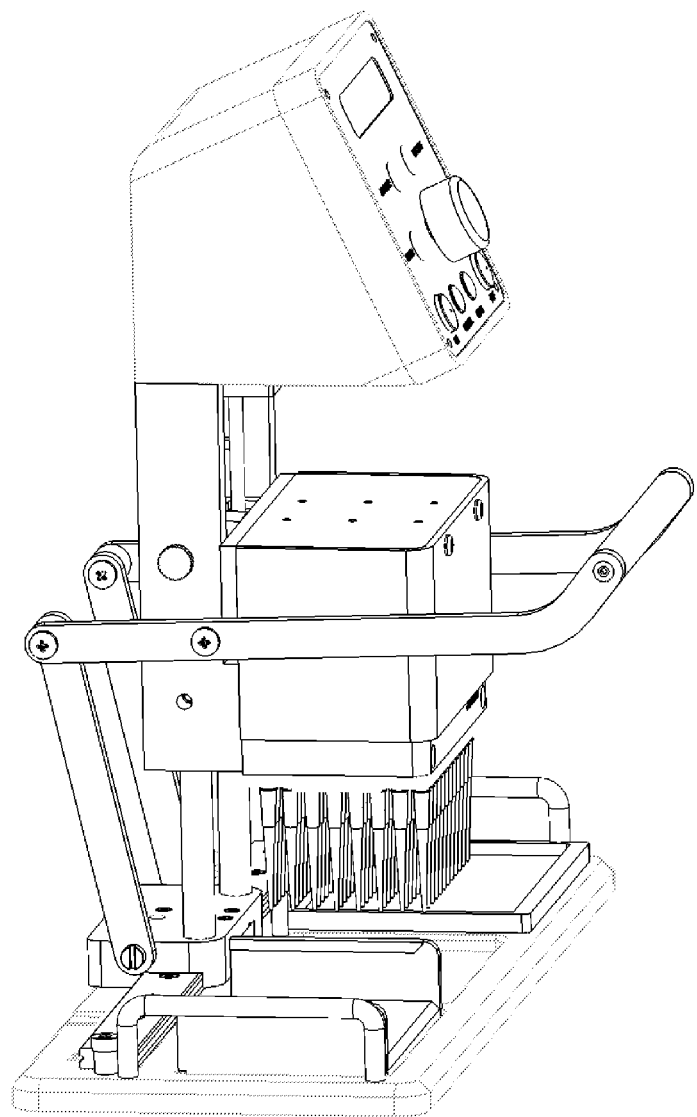
Figure 23:
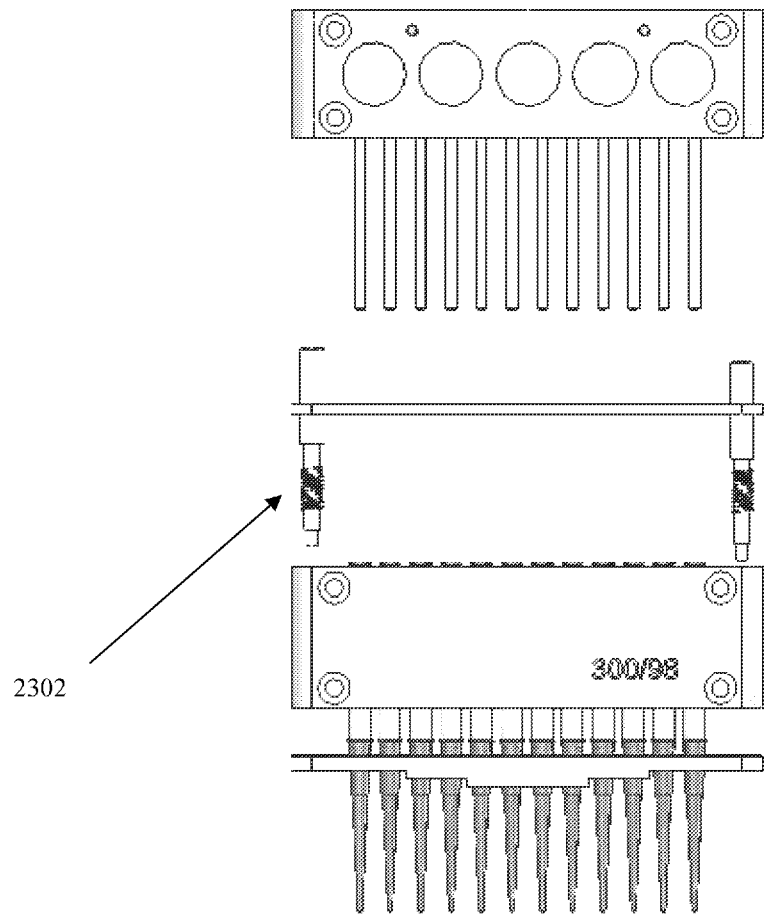
Figure 24:
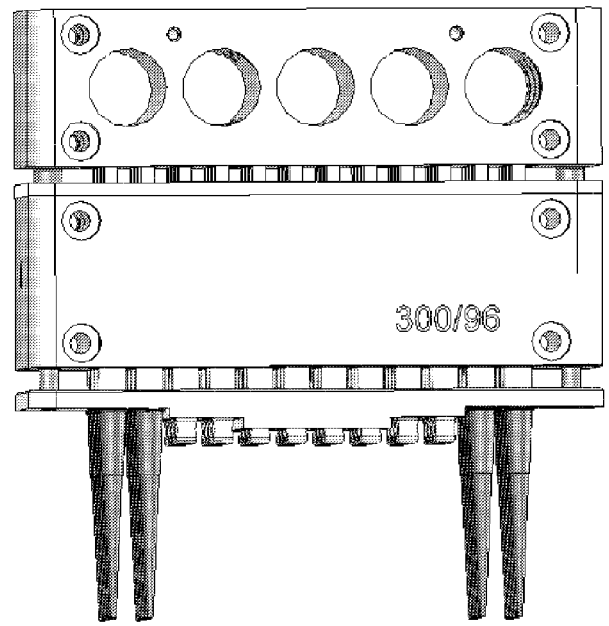
Figure 25:
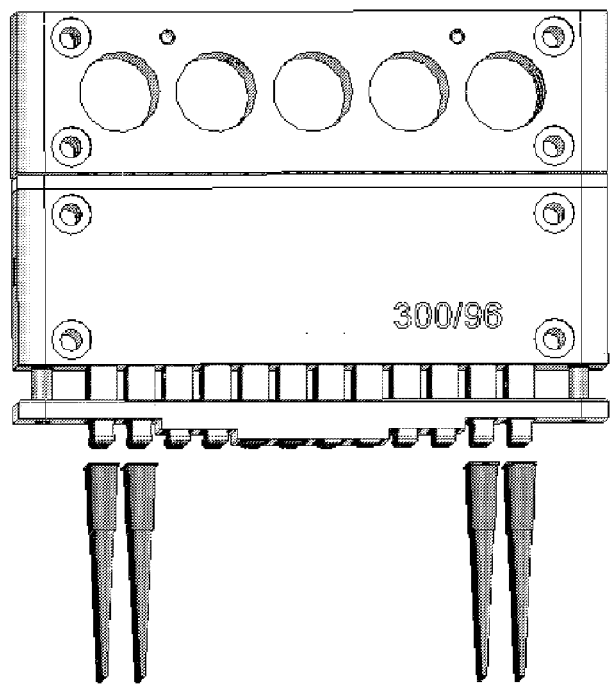
Figure 26:
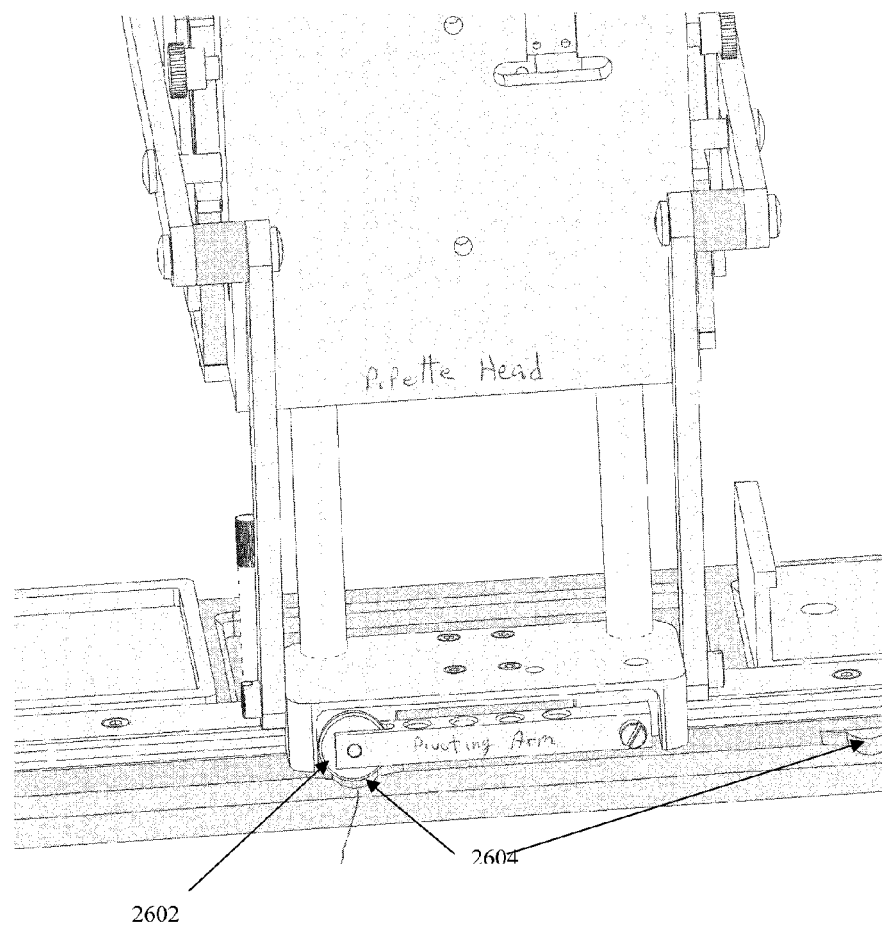

Another method of designing the 96/384 adaptor 2100 is to make the bottom footprint of the adaptor 4.5 mm smaller in both the X & Y directions, see FIG. 21. This way both the adaptor & plate move together while sliding in the standard station well below. This design will move exactly like the first design to access the four wells in the 384 plate, except this time the adaptor moves and the plate is an exact fit on the top side of the adaptor.

Using the concept of the two adaptor designs described above, but this time with a 384 channel pipettor, one can adapt to a 1536 plate. This adaptor has a 2.25 mm offset to allow travel from one 1536 well to the other. Refer to the attached ANSI_SBS_4 "Microplate Well Positions" for details and illustrations of the 96, 384 & 1536 plates.

A rotating handle is used to move the upper portion up and down with extreme ease and precision. The upper head assembly may be in the upper or lower positions. The lower is called the "positive stop position". The two illustrated adjustable stops (1920, 1922) allow the user to either screw the knurled portion up or down to set a repeatable height at which the upper unit will stop at every time. This allows the user to quickly pull the head down until it stops against the stop, thus eliminating the need to visually gauge the proper lower height.

The handle rotates about a fixed axis to give the user a smooth mechanical advantage when adjusting the upper height position. The pivoting handle transfers vertical motion (force) nearly directly over the two vertical fixed shafts, thus eliminating a moment force that tends to bind with motion. Furthermore, this handle provides a mechanical advantage to reduce force needed to move the upper unit up and down. Also the handle is now positioned further away from the three position wells below, eliminating potential contamination from the users hand to the product being pipetted into below.

The custom "pivoting arm & wheel" 2602 provides positive yet smooth feedback to the user to center the upper unit directly over the desired well 2604 below. Three position can be used, where a microplate, reservoir, tip box or whatever may appear, sliding the upper unit to a precise position over each position below is easily accomplished by the self centering wheel engaging with the mating detent.

Various embodiments and features of the present invention have been described in detail with a certain degree of particularity. The utilities thereof can be appreciated by those skilled in the art. It should be emphasized that the above-described embodiments of the present invention merely describe possible examples of the implementations to set forth a clear understanding of the principles of the invention, and that numerous changes, variations, and modifications can be made to the embodiments described herein without departing from the spirit and scope of principles of the invention. Also, such variations and modifications are intended to be included herein within the scope of the present invention, as set forth in the appended claims. The scope of the present invention is defined by the appended claims, rather than the forgoing description of embodiments. Accordingly, what is desired to be secured by Letters Patent is the invention as defined and differentiated in the following claims, and all equivalents.

I claim:

1. A pipette holding apparatus for simultaneously holding eight or more pipette tips comprising;
    an upper stationary fitting;
    a pull/push rod having axial movement in/out of the fitting;
    a compliant tapered head receiver;
    mechanical means for pulling on said rod, so that when the rod pushes on the head, its diameter expands outward into the pipettes' internal surface, forming a continuous annular seal;
    mechanical means for pushing on said rod;
    the compliant tapered head receiver has one or more slits cut along a portion of its side;
    the pull/push rod has a tapered head at least one end;
    wherein said upper stationary fitting is comprised of 96 or more pipette fittings; and
    a manually powered ejector plate to simultaneously eject all 96 or more said pipette tips.

2. A pipette holding apparatus for simultaneously holding eight or more pipette tips comprising;
    a Ferro fluidic taper expansion with a magnetic field, and magnetic means to radially expand said Ferro fluidic filled lower tapered fitting so that an annular shape is formed in said taper that makes continuous contact with a pipette's internal surface at the proximal end of said pipette.

* * * * *